United States Patent
Koenig et al.

(10) Patent No.: US 10,241,081 B2
(45) Date of Patent: Mar. 26, 2019

(54) SENSORY ELEMENTS FOR PULSED EDDY CURRENT PROBE

(71) Applicants: Kamalu Michael-Stanley Koenig, Centennial, CO (US); Owen Michael Malinowski, Gilbertsville, PA (US)

(72) Inventors: Kamalu Michael-Stanley Koenig, Centennial, CO (US); Owen Michael Malinowski, Gilbertsville, PA (US)

(73) Assignee: Structural Integrity Associates, Inc., San Jose, CA (US)

( * ) Notice: Subject to any disclaimer, the term of this patent is extended or adjusted under 35 U.S.C. 154(b) by 0 days.

(21) Appl. No.: 15/187,142

(22) Filed: Jun. 20, 2016

(65) Prior Publication Data

US 2017/0363579 A1 Dec. 21, 2017

(51) Int. Cl.
*G01N 27/90* (2006.01)

(52) U.S. Cl.
CPC .................................. *G01N 27/904* (2013.01)

(58) Field of Classification Search
None
See application file for complete search history.

(56) References Cited

U.S. PATENT DOCUMENTS

| | | | | |
|---|---|---|---|---|
| 8,593,137 B2* | 11/2013 | Ide | | G01N 27/90 324/225 |
| 2004/0245997 A1* | 12/2004 | Plotnikov | | G01N 27/904 324/529 |
| 2005/0062470 A1* | 3/2005 | Shoji | | G01N 27/9033 324/240 |
| 2005/0122100 A1* | 6/2005 | Wan | | G01R 33/0206 324/247 |
| 2007/0080682 A1* | 4/2007 | Govari | | A61B 5/06 324/247 |
| 2010/0007342 A1* | 1/2010 | Lepage | | G01N 27/902 324/240 |
| 2012/0206132 A1* | 8/2012 | Lepage | | G01N 27/9033 324/239 |
| 2012/0330491 A1* | 12/2012 | Olinger | | G05D 1/0261 701/23 |
| 2013/0038321 A1* | 2/2013 | Suzuki | | G01R 35/00 324/224 |
| 2013/0076348 A1* | 3/2013 | Ide | | G01N 27/90 324/232 |

OTHER PUBLICATIONS

Shen Wang et al.; Chapter 2 The Pulsed Eddy Current Testing; Tsinghua University Press, Beijing; 2013; pp. 41, 50-51 and 69-73. (Year: 2013).*

* cited by examiner

*Primary Examiner* — Melissa J Koval
*Assistant Examiner* — Nasima Monsur
(74) *Attorney, Agent, or Firm* — Seth L. Hudson; Clements Bernard Walker, PLLC

(57) ABSTRACT

The present invention provides methods and systems for sensory elements for placement within a probe that includes at least one receiving coil disposed within a pulsed eddy current probe, and at least one sensing element disposed within a pulse eddy current probe. The at least on sensing element may be disposed on a printed circuit board.

5 Claims, 7 Drawing Sheets

SENSORY ELEMENTS FOR PULSED EDDY CURRENT PROBE

CROSS REFERENCE TO RELATED PATENT APPLICATION

The present patent application/patent claims the benefit of priority of U.S. Provisional Patent Application No. 62/181,878, filed on Jun. 19, 2015, and entitled "MULTIPLE SENSING ELEMENT CONFIGURATIONS FOR PULSED EDDY CURRENT PROBE," the contents of which are incorporated in full by reference herein.

FIELD OF THE INVENTION

The present invention relates generally to sensory elements for pulsed eddy current probes, and more generally relates to arrangements of multiple receiving coils and sensing elements designed to decouple variations in material properties, probe liftoff, and/or remaining wall thickness of the test specimen.

BACKGROUND OF THE INVENTION

Eddy current testing is a technique that can be used to determine the presence of flaws, such as cracks, in a specimen composed of conductive materials. Eddy current testing utilizes electromagnetic induction, where a coil of a probe is placed proximate to a test specimen that is formed from conductive materials. The coil is energized via a current to create a magnetic field. The magnetic field induces eddy currents in the conductive materials of the test specimen, which generate a secondary magnetic field. The nature of the secondary magnetic field, such as its magnitude or directionality, at least partially depends on the structural features of the test specimen. For example, cracks, dents, or other structural irregularities may induce perturbations in the secondary magnetic field.

The secondary magnetic field is also affected by probe liftoff and changes in the material properties of the test specimen, for example magnetic permeability, electrical conductivity, and residual magnetization. These probe liftoff and material property variations, if unaccounted for, can result in false positive or false negative indications of wall loss.

BRIEF SUMMARY OF THE INVENTION

The present invention is a series of multiple sensing element configurations for a pulsed eddy current sensor which facilitate decoupling of variations in probe liftoff, test specimen thickness, and test specimen material properties.

According to an embodiment of the present invention, the method is applied to dynamic pulsed eddy current measurements.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

A probe as described in U.S. patent application Ser. No. 15/041,447 may be used with the present invention and is incorporated herein by reference. The probe is generally designed for the nondestructive examination of electrically conductive materials using a dynamic pulsed eddy current technique while simultaneously scanning and acquiring data on the specimen. The probe may include at least two magnetizing yokes—a first magnetizing yoke and a second magnetizing yoke. A coil is positioned around a portion of the first magnetizing yoke and second magnetizing yoke, and at least one sensor array may disposed within the coil.

Figure 1:
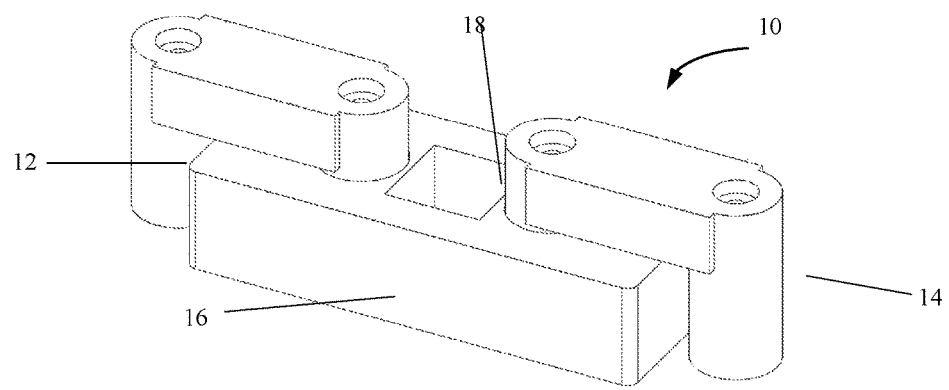
FIG. 1 is a perspective view of an exemplary pulsed eddy current probe.

Referring now specifically to the drawings, an exemplary dynamic eddy current probe is illustrated in FIG. 1 and is shown generally at reference numeral 10. The probe 10 is generally designed for the nondestructive examination of electrically conductive materials using a dynamic pulsed eddy current technique while simultaneously scanning and acquiring data on the specimen. The probe 10 includes at least two magnetizing yokes—a first magnetizing yoke 12 and a second magnetizing yoke 14. A generation coil 16 is positioned around a portion of the first magnetizing yoke 12 and second magnetizing yoke 14, and at least one sensor array 18 or other receiving element is disposed within an opening within the coil assembly 16.

Figure 2:
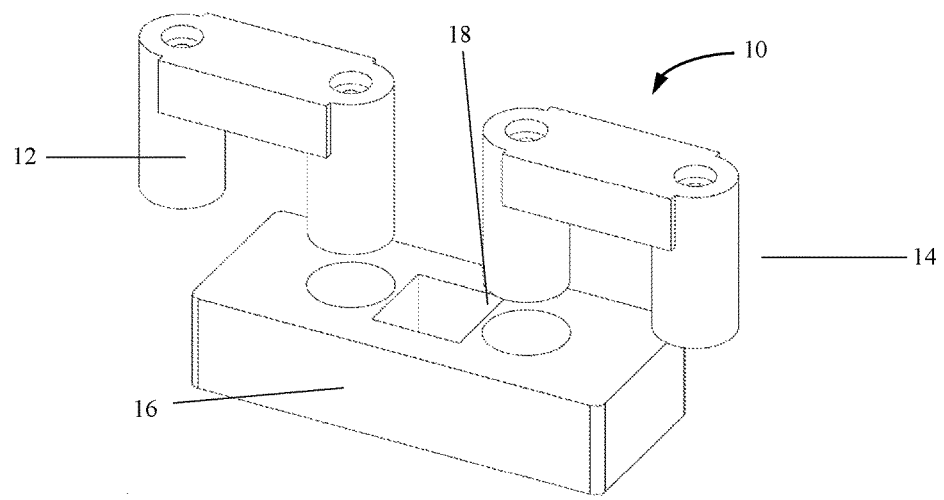
FIG. 2 is an exploded view of the exemplary pulsed eddy current probe as shown in FIG. 1.

The first magnetizing yoke 12 and second magnetizing yoke 14, as shown in FIGS. 1 and 2, are substantially u-shaped. In other words, the magnetizing yokes 12, 14 have a first leg and a second leg that are connected by a top portion with each leg extending generally downwardly from the top portion. An interior cavity is formed between the inner sides of the first leg, second leg, and top portion. The first leg and top portion of the magnetizing yokes 12, 14 form substantially a portion of the exterior of the probe 10. In the exemplary embodiment of FIGS. 1 and 2, the probe 10 consists of the first magnetizing yoke 12 and the second magnetizing yoke 14 disposed in a spaced-apart relationship. The second leg of each magnetizing yoke 12, 14 is disposed adjacent each other and in a spaced-apart relationship.

The yokes 12, 14, as shown in FIGS. 1 and 2, have a generally cylindrical first leg and second leg having a first end, a second end, and an external surface. The top portion connects the second end of the first leg and the second end of the second leg. The top portion extends downwardly from the second end of the first leg and the second end of the second leg and continues partially along the external side of the first leg and second leg. The yokes 12, 14 also may contain a recessed bore disposed on the second end of the first leg and second end of the second leg. The recessed bore may also contain a shelf positioned therein. The recessed bore may be circular that corresponds with a circular shelf, as the recessed bore continues downwardly from the circular shelf.

The yokes 12, 14 are selectively secured to the coil assembly 16, wherein the second leg of the first yoke 12 and the second leg of the second yoke 14 are engaged to the coil assembly 16. The generation coil 16 contains a pair of positioning bores for receiving the second leg of the first yoke 12 and the second leg of the second yoke 14. The second leg of the first yoke 12 and the second leg of the second yoke 14 may be engaged within the positioning bores or selectively secured within the positioning bores. The positioning bores correspond to the shape of the second leg of the yokes 12, 14. As illustrated in FIGS. 1 and 2, the positioning bores are circular to correspond with the circular second leg of the yokes 12, 14, wherein the diameter of the positioning bore is slightly larger than the diameter of the second leg of the yokes 12, 14.

A generation coil 16 may be positioned within the inner cavity of the probe 10 and may be adjacent the interior side of the first leg and the second leg of the magnetizing yokes 12, 14. The generation coil 16, as shown in FIG. 2, is positioned within the cavity of the two magnetizing yokes 12, 14 and disposed adjacent the interior side of the second leg of each magnetizing yoke 12 14. The generation coil 16 is continuous and partially encircles the second leg of the first magnetizing yoke 12 and the second leg of the second magnetizing yoke 14 and engaging the first magnetizing yoke 12 to the second magnetizing yoke 14. The generation coil 16, driven by a current pulse, subsequently generates and transmits a primary transient magnetic field that induces transient eddy currents into the conductive specimen. These transient eddy currents generate a secondary transient magnetic field within the conductive specimen.

The at least one sensor array 18 may be positioned within an opening in the probe 10 or coil assembly. As shown in FIGS. 1 and 2, the at least one sensor array 18 is disposed near the exterior sides of the second leg of the first magnetizing yoke 12 and the second magnetizing yoke 14. As illustrated, an opening is formed within the generation coil 16 for allowing a single sensor array 18 to be disposed within the opening of the generation coil 16. In this arrangement, the second leg of the first magnetizing yoke 12 and the second leg of the second magnetizing yoke 14 provide a shielding effect for shielding the sensor array 18 from the field. The sensor array 18 is oriented with its sensitive axis normal or parallel to the surface of the conductive specimen on which the probe is placed and tasked to analyze.

In a scanning pulsed eddy current application, there are two sources of eddy currents within the electrically conductive specimen: transient eddy currents induced by the primary transient magnetic field and eddy currents induced by the motion of the probe. The eddy currents induced by motion will produce perturbations on the secondary transient magnetic field. These perturbations could be detected as false positives by the scanning probe. The value of the magnetic Reynolds of the probe determines which eddy current induction mechanism dominates. A minimal magnetic Reynolds number restricts the extent to which eddy currents due to the motion of the probe are generated. The probe 10 was designed to minimize its magnetic Reynolds number with a shorter length in the scanning direction. This ensures that the signal measured by the probe 10 while scanning is dominated by the secondary transient magnetic field and that the eddy currents induced by the motion of probe 10 have little to no influence on the received signal. The shorter dimension in the scanning direction allows the probe 10 to simultaneously scan and acquire data on the specimen. In addition, the shorter dimension results in a lower sensor-lift-off when scanning a pipe from the ID surface with the long axis of the probe 10 in the pipe's axial direction. The magnetizing yokes 12, 14 may be constructed of ferrite to further concentrate the magnetic field of the coil.

In an alternative embodiment, the probe 110 includes a first magnetizing yoke 112, a second magnetizing yoke 114, a third magnetizing yoke 116, and a fourth magnetizing yoke 118. A coil assembly 120 is positioned around a portion of the first magnetizing yoke 112, the second magnetizing yoke 114, the third magnetizing yoke 116, and the fourth magnetizing yoke 118, and at least one sensor array 122 is disposed within the coil assembly 120.

Figure 3:
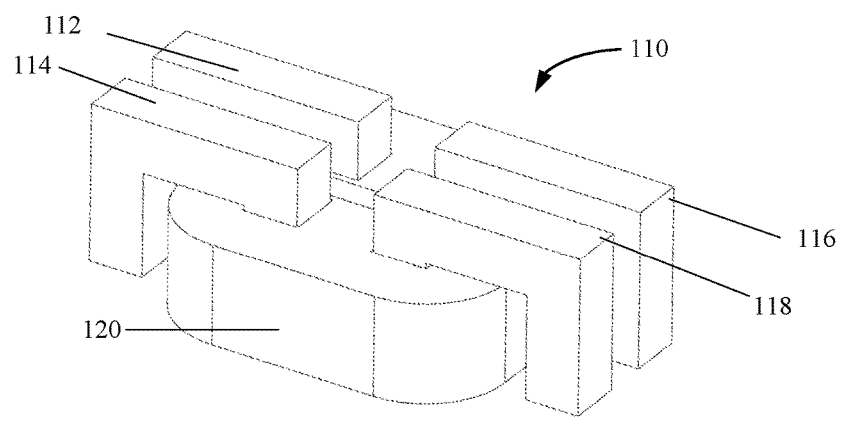
FIG. 3 is a perspective view of another embodiment of an exemplary pulsed eddy current probe.

The magnetizing yokes 112, 114, 116, and 118, as shown in FIG. 3, are substantially u-shaped as described above. The first leg and top portion of the magnetizing yokes 112, 114, 116, and 118 form substantially a portion of the exterior of the probe 110. In the exemplary embodiment of FIGS. 3 and 4, the probe 110 consist of first magnetizing yoke 112 and second magnetizing yoke 114 disposed in a spaced-apart side-by-side relationship. The third magnetizing yoke 116 and fourth magnetizing yoke 118 are disposed within a spaced-apart side-by-side relationship.

The magnetizing yokes 112, 114, 116, and 118 contain a first leg and a second leg. The second leg of the first magnetizing yoke 112 is disposed adjacent the second leg of the third magnetizing yoke 116, and the second leg of the second magnetizing yoke 114 is disposed adjacent the second leg of the fourth magnetizing yoke 118. The second let of the magnetizing yokes 112, 114, 116, and 118 are partially positioned within the generation coil 120.

The generation coil 120 is positioned within the inner cavity of the probe 10 formed between the first and second legs of the magnetizing yokes 112, 114, 116, and 118. The generation coil 120 is adjacent the interior side of the first leg and second leg of the magnetizing yokes 112, 114, 116, 118. The generation coil 120 is preferably composed of copper.

Figure 4:
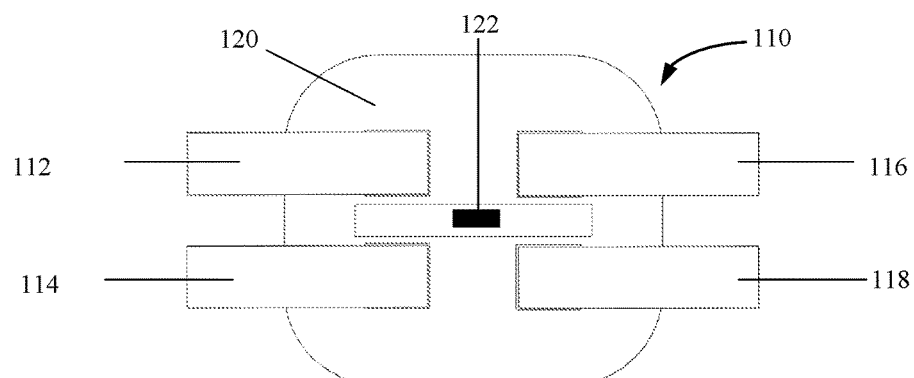
FIG. 4 is a top view of the embodiment of the exemplary pulsed eddy current probe as shown in FIG. 3.

The at least one sensor array 122 is disposed within the generation coil 120. As shown in FIG. 4, the at least one sensor array 122 is centrally located within the generation coil 120 and disposed adjacent the exterior sides of the second leg of the magnetizing yokes 112, 114, 116, and 118. As illustrated, an opening is formed within the generation coil 120 for allowing a single sensor array 122 to be disposed within the opening of the generation coil 120. As illustrated in FIG. 4, the sensor array 122 is a one-dimensional sensor array. However, additional sensor arrays 122 may be disposed within the probe 110 for creating a two-dimensional or three-dimensional sensor array.

Figure 5:
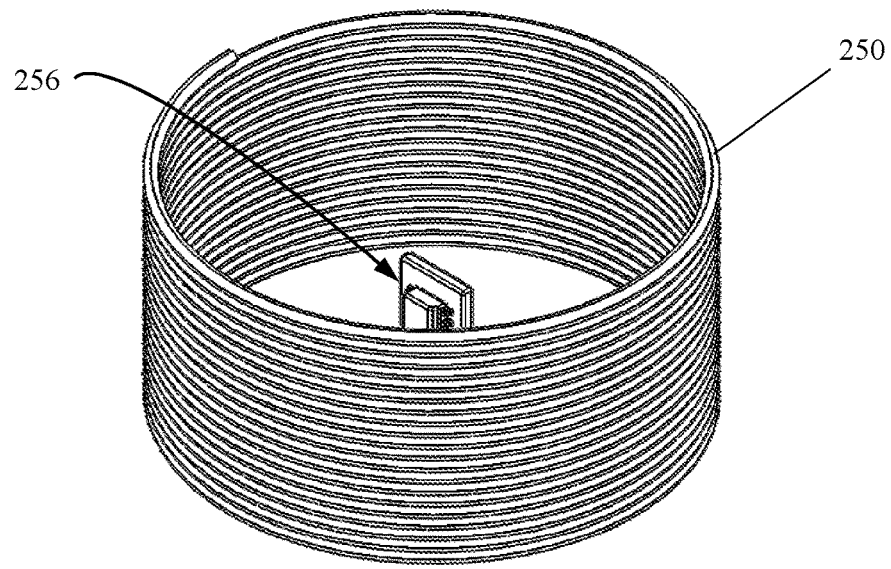
FIG. 5 is a top perspective view of a sensing element within a coil.
Figure 6:
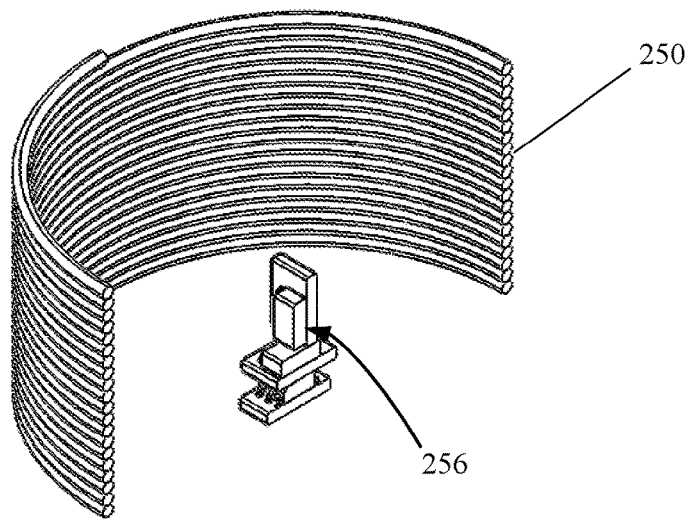
FIG. 6 is a cut-away view of a sensing element within a coil.
Figure 9:
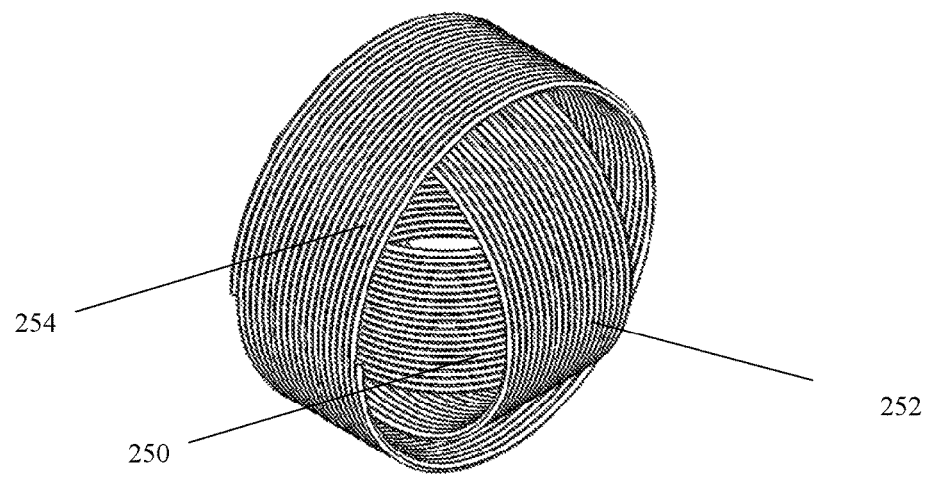
FIG. 9 is a top perspective view of an embodiment of the coil of the present invention.
Figure 10:
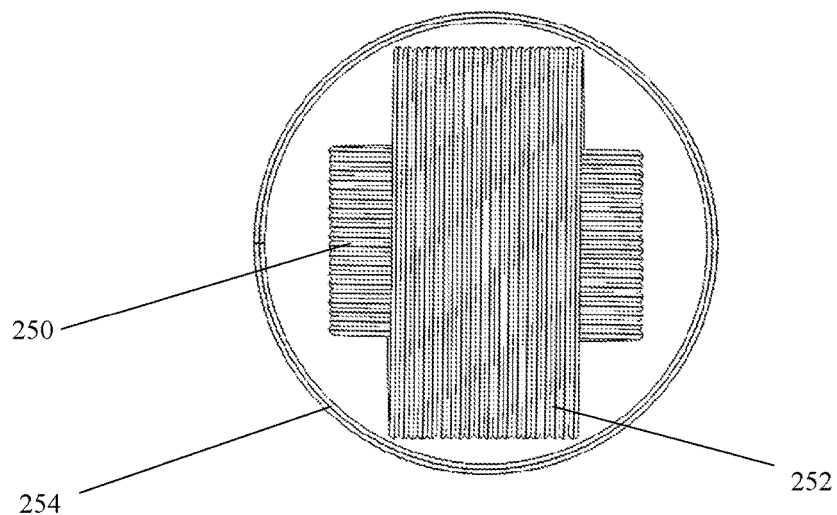
FIG. 10 is a top view of an embodiment of the coil of the present invention.

As illustrated in FIGS. 5 and 6, at least one receiving coil, hereinafter referred to as the first receiving coil 250, may be disposed within a probe 10. Additionally, a sensing element 256 may be disposed within the first receiving coil 250. Additionally and as illustrated in FIGS. 5 and 6, multiple sensing elements 256 may be disposed within a probe 10 having a plurality of configurations. As illustrated in FIGS. 9 and 10, a coil assembly is depicted and contains a first receiving coil 250 aligned in the x-axis, a second receiving coil 252 aligned in the y-axis, and a third receiving coil 254 aligned in the z-axis. It is within the scope of the present invention that only the first receiving coil 250 and the second receiving coil 252 may be positioned within the probe 10. Generally, the x-axis is the scanning direction of the probe 10, and the first receiving coil 250 is positioned in the x-direction. For clarification, positioned in the x-direction means the first receiving coil 250 is wound along the x-axis or in the direction of the x-axis with its sensitive axis being the x-axis. The second receiving coil 252 is wound over and around the first receiving coil 250, preferably without contacting or touching the first receiving coil 250. The second receiving coil 252 is wound along the y-axis with its sensitive axis being the y-axis. As illustrated, the second receiving coil 252 is wound over the first receiving coil 250, but it should be noted that the second receiving coil 252 may also be positioned within the first receiving coil 250. The third receiving coil 254 is wound over and around the second receiving coil 252, preferably without contacting or touching the second receiving coil 252. The third receiving coil 254 is wound along the z-axis with its sensitive axis being the z-axis.

Preferably, the first receiving coil 250 may be wrapped in a form, preferably plastic, for stabilizing and reinforcing the first receiving coil 250. In embodiments containing the second receiving coil 252 and third receiving coil 254, the receiving coils (252, 254) are also engaged to the form. The receiving coils 250, 252, 254 are placed within the generation coil 16, as illustrated in FIGS. 1-4. The generation coil 16 has an opening therein for receiving at least one of the receiving coils 250, 252, 254.

A sensor array is illustrated in FIGS. 6-8 and 11-13. The sensor array includes at least one sensing element 256 that may be disposed within a receiving coil 250, 252, 254 or may be placed within an opening within the generation coil 16 without one of the receiving coils 250, 252, 254. The sensor array containing at least one sensing element 256 may be centrally located within the first receiving coil 250 as illustrated in FIGS. 5 and 6. A cavity is formed within the first receiving coil 250 for allowing a sensing element 256 to be disposed within the cavity. The sensing element 256 may be one-dimensional. However, additional sensing elements 256 may be disposed within the probe 10 for creating a two-dimensional or three-dimensional array.

Figure 7:
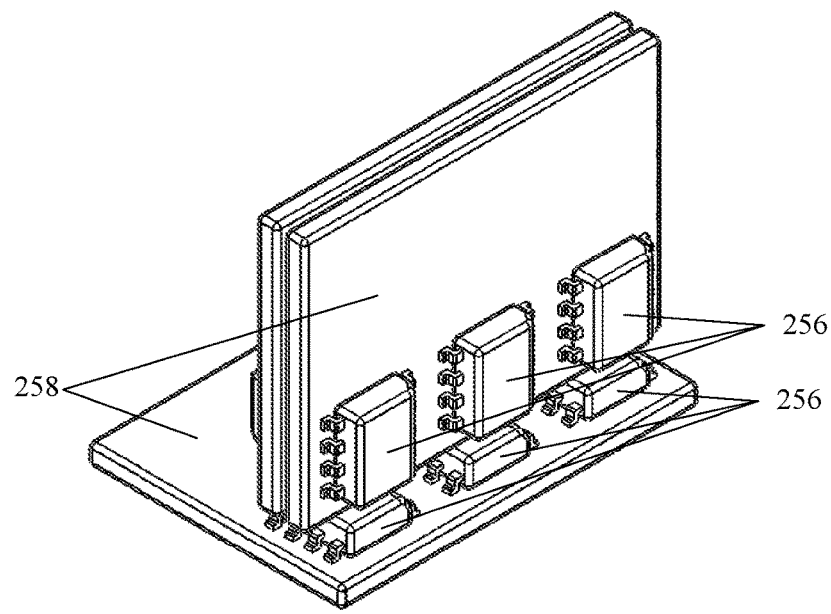
FIG. 7 is one embodiment of a sensing element of the present invention.
Figure 8:
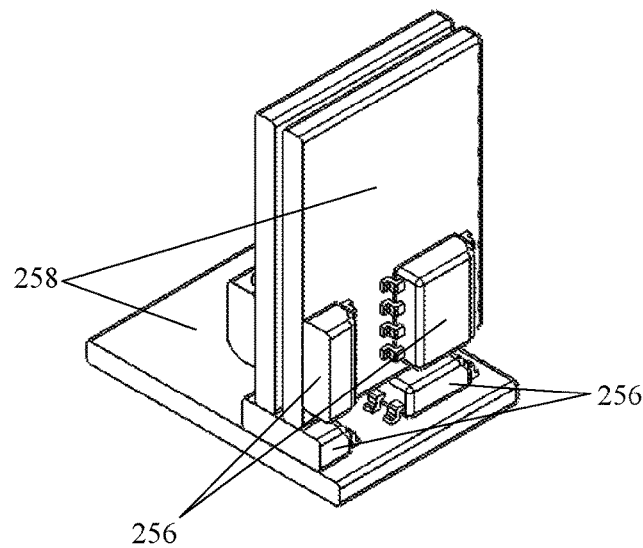
FIG. 8 is a side view of another embodiment of a sensing element of the present invention.

As illustrated in FIGS. 6-8 and 11-13, a sensing elements 256 arranged in arrays are disposed on a circuit board 258, such as a printed circuit board (PCB), for orienting the sensing element 256 and therefore the sensor array in a specific orientation. As illustrated in FIGS. 7 and 8, three sensing elements 256 are disposed on a circuit board 258 and oriented in the horizontal position or x-axis. Three sensing elements 256 are disposed on a first vertical circuit board 258, and three sensing elements 256 are positioned on a second vertical circuit board 258. The first and second vertical circuit boards 258 are oriented in the vertical position or y-axis. As illustrated in FIG. 6, three sensing elements 256 are disposed on a circuit board 258 and oriented in the vertical position or x-axis. Three sensing elements 256 are disposed on a first horizontal circuit board 258, and three sensing elements 256 are positioned on a second horizontal circuit board 258. The first and second horizontal circuit boards 258 are oriented in the horizontal position or x-axis. It should be noted that it is in the purview of the present invention to have one or more sensing elements 256 disposed on the circuit board 258, and that the array may consist of one circuit board 258 in the horizontal direction and one circuit board in the vertical direction.

Figure 11:
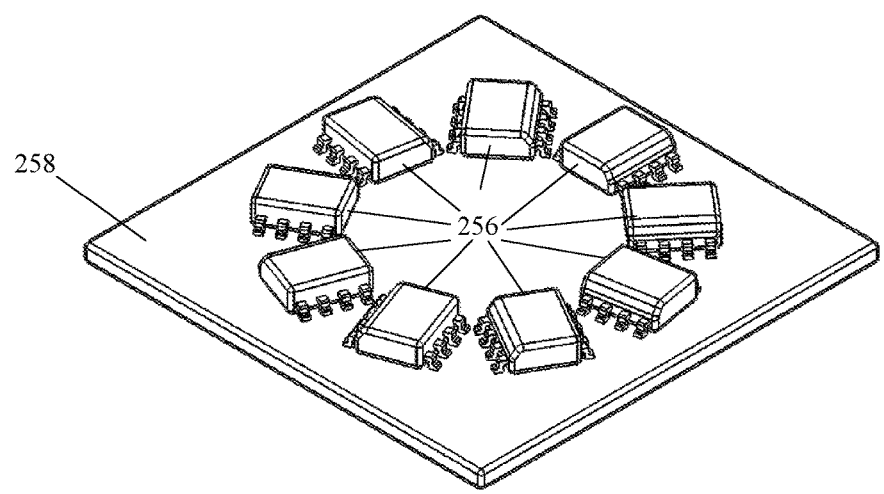
FIG. 11 is a top perspective view of another embodiment of the sensing elements of the present invention.

As illustrated in FIG. 11, a sensor array is shown with a plurality of sensing elements 256 arranged in a circular pattern on the top side of the circuit board 258. The sensing elements 256 are in a spaced-apart relationship and oriented such that a circular void is formed by the sensing elements 256. The sensing elements have a first side and a second side, wherein in this embodiment, the first side of the sensing element 256 faces the center of the circuit board 258 and the second side faces outward to the edge of the circuit board 258. Each sensing element 256 is in a spaced-apart relationship with the adjacent sensing element 256 and each sensing element 256 is placed at an angle with respect to the adjacent sensing element 256, wherein the plurality of sensing elements 256 form a circular pattern, thus creating a circular void on the printed circuit board 258 between the first side of each sensing elements 256. Ideally, the circuit board 258 in this arrangement would be arranged on a plane in the probe 10 parallel to the test material.

Figure 12:
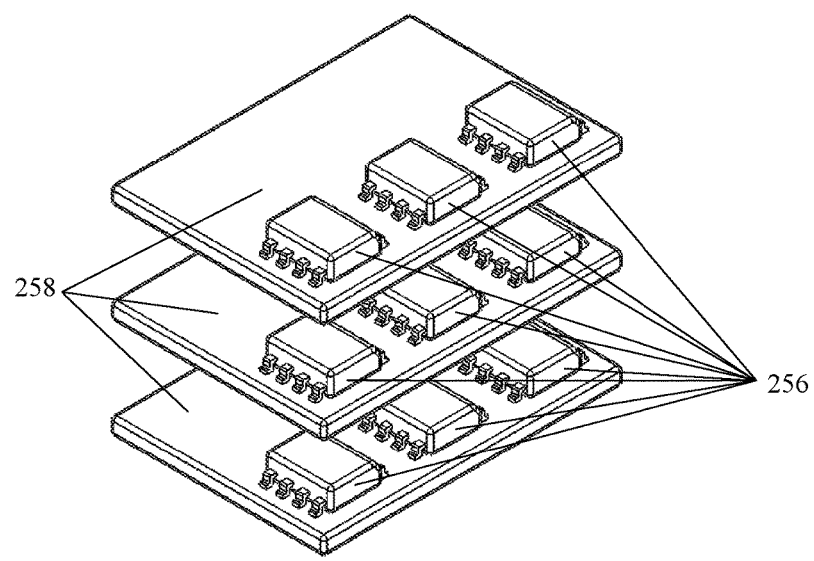
FIG. 12 is a top perspective view of another embodiment of the sensing elements of the present invention.
Figure 13:
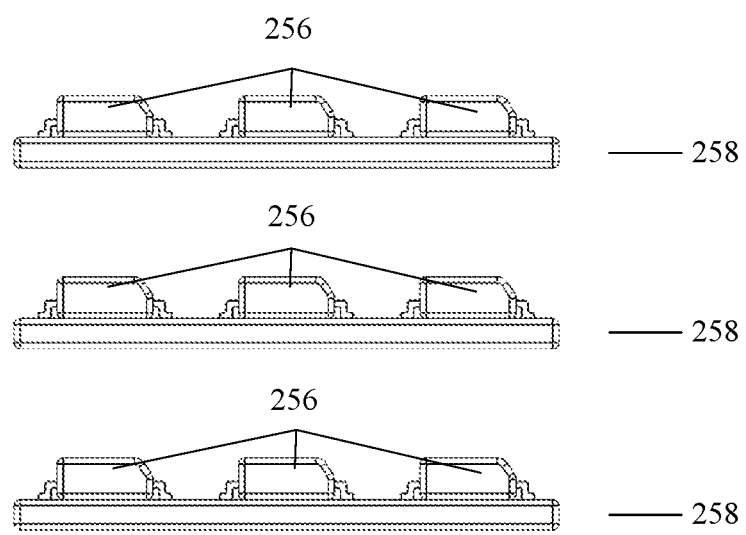
FIG. 13 is a side view of another embodiment of the sensing elements of the present invention.

As illustrated in FIGS. 12 and 13, three circuit boards 258 are arranged in a spaced-apart, stacked relationship, wherein each of the circuit boards 258 are positioned on top of each other. Three sensing elements 256 are disposed on the top portion of each circuit board 258. The sensor arrays can be oriented parallel or perpendicular to the test material in the probe 10.

The sensing elements 256 may be multiplexed and sampled simultaneously. The sending elements 256 may also be a giant magnetoresistor, a tunneling magnetoresistor and/or a Hall Effect Sensor.

Ideally, the arrays are potted in an epoxy compound. The epoxy compound would encompass the sensing elements 256 and circuit boards 258 of the array. The requisite wiring would extend from the array and outside the epoxy.

The sensitive axis of the receiving coils 250, 252, 254 and sensing element 256 may be oriented perpendicular to the surface of the test specimen, parallel to the surface of the test specimen, or a combination thereof within the probe 10. Multiple parallel sensing elements may be oriented orthogonally with respect to one another and/or with respect to the sensing element(s) oriented perpendicular to the test specimen. These configurations are designed to measure the secondary magnetic field generated in the test specimen in one, two, or three component directions with respect to customary coordinate axes.

The multiple receiving coils 250, 252, 254 and sensing elements 256 are configured so as to facilitate isolation of the measurement of one or more physical quantities, which may include pulsed eddy current probe liftoff, test specimen wall loss, and/or test specimen material properties. The material properties may include, for example, magnetic permeability, electrical conductivity, residual magnetization, etc. The multiple sensing elements may isolate the measurements of one or more physical quantities by comparison of the signals of the multiple sensing elements, or by arrangement of one or more of the sensing elements such that the sensing element is indifferent or resistant to variations in one or more of the physical quantities.

A digital signal processing method compares the received signals from the receiving coils 250, 252, 254 or sensing element 256 of the pulsed eddy current probe 10 to isolate variations in one or more physical quantities, as previously described. The processing method may compare the signals themselves through, for example, signal subtraction, signal division, or cross correlation. The processing scheme may also compare one or more features extracted from the receiving coils 250, 252, 254 or sensing element 256. The features may be extracted from, for example, the time domain or the frequency domain signals.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. Sensory elements for placement within a pulsed eddy current probe, comprising:
    a first receiving coil and a second receiving coil that is wound over and around the first receiving coil and at least one sensing element disposed on a circuit board within a cavity of the receiving coils between the first receiving coil and the second receiving coil; the pulsed eddy current probe, comprising:
    a first magnetizing yoke having a first leg and a second leg with each leg having an interior side and an exterior side;
    a second magnetizing yoke having a first leg and a second leg with each leg having an interior side and an exterior side;
    an inner cavity formed within the interior side of the second leg and the first leg of the first magnetizing yoke and the interior side of the second leg and the first leg of the second magnetizing yoke;
    a coil assembly comprising a generation coil positioned within the inner cavity and a pair of positioning bores, wherein the second leg of each of the at least two magnetizing yokes is positioned within the pair of positioning bores of the coil assembly, the generation coil contains an opening; and
    the first receiving coil, the second receiving coil and at least one sensing element disposed on the circuit board and within the opening of the generation coil.

2. The sensory elements for placement within a probe according to claim 1, further comprising at least one circuit board positioned in the vertical direction for receiving at least one sensing element and at least one circuit board positioned in the horizontal direction for receiving at least one sensing element.

3. The sensory elements for placement within a probe according to claim 1, further comprising a third receiving coil and the sensing element is disposed within the cavity of the first receiving coil.

4. The sensory elements consist of a first receiving coil, a second receiving coil, and a third receiving coil according to claim 3, wherein the first receiving coil is disposed on an x-axis that is aligned with the plane for scanning by the probe, the second receiving coil is disposed on the y-axis, and the third receiving coil is disposed on the z-axis.

5. The sensory elements consist of a first receiving coil, a second receiving coil, and a third receiving coil according to claim 3, wherein the second receiving coil is spaced-apart and surrounds the first receiving coil and the third receiving coil is spaced-apart and surrounds the second receiving coil.

\* \* \* \* \*